US011311482B2

(12) United States Patent
Angel et al.

(10) Patent No.: US 11,311,482 B2
(45) Date of Patent: Apr. 26, 2022

(54) TOPICAL COMPOSITIONS AND METHODS FOR TREATING SKIN DISEASES

(71) Applicant: BAUSCH HEALTH US, LLC, Bridgewater, NJ (US)

(72) Inventors: Arturo Angel, Santa Rosa, CA (US); Radhakrishnan Pillai, Santa Rosa, CA (US)

(73) Assignee: BAUSCH HEALTH US, LLC, Bridgewater, NJ (US)

( * ) Notice: Subject to any disclaimer, the term of this patent is extended or adjusted under 35 U.S.C. 154(b) by 0 days.

(21) Appl. No.: 16/179,561

(22) Filed: Nov. 2, 2018

(65) Prior Publication Data

US 2019/0133942 A1 May 9, 2019

Related U.S. Application Data

(63) Continuation-in-part of application No. 15/977,088, filed on May 11, 2018, now abandoned.

(60) Provisional application No. 62/505,421, filed on May 12, 2017.

(51) Int. Cl.
| | |
|---|---|
| *A61K 9/107* | (2006.01) |
| *A61K 9/00* | (2006.01) |
| *A61P 17/00* | (2006.01) |
| *A61K 31/4436* | (2006.01) |
| *A61K 47/34* | (2017.01) |
| *A61K 47/14* | (2017.01) |
| *A61K 47/44* | (2017.01) |
| *A61P 17/10* | (2006.01) |
| *A61K 9/06* | (2006.01) |
| *A61K 47/06* | (2006.01) |
| *A61K 47/32* | (2006.01) |

(52) U.S. Cl.
CPC ............ *A61K 9/107* (2013.01); *A61K 9/0014* (2013.01); *A61K 9/06* (2013.01); *A61K 31/4436* (2013.01); *A61K 47/06* (2013.01); *A61K 47/14* (2013.01); *A61K 47/32* (2013.01); *A61K 47/34* (2013.01); *A61K 47/44* (2013.01); *A61P 17/00* (2018.01); *A61P 17/10* (2018.01)

(58) Field of Classification Search
USPC ....................................................... 514/337
See application file for complete search history.

(56) References Cited

U.S. PATENT DOCUMENTS

| | | | |
|---|---|---|---|
| 6,730,308 B1 | 5/2004 | Sefton | |
| 8,808,716 B2 | 8/2014 | Loupenok | |
| 10,251,895 B2 | 4/2019 | Dow et al. | |
| 10,426,787 B2 | 10/2019 | Dow et al. | |
| 2012/0129824 A1 | 5/2012 | Angel et al. | |
| 2012/0328670 A1* | 12/2012 | Donello | A61K 9/0014 |
| | | | 424/400 |
| 2014/0349981 A1 | 11/2014 | Evers et al. | |
| 2016/0367570 A1 | 12/2016 | Dow et al. | |
| 2018/0177803 A1 | 6/2018 | Dow et al. | |
| 2018/0360752 A1 | 12/2018 | Arturo et al. | |
| 2019/0133943 A1 | 5/2019 | Arturo et al. | |
| 2019/0231797 A1 | 8/2019 | Dow et al. | |
| 2021/0145847 A1 | 5/2021 | Dow et al. | |
| 2021/0330681 A1 | 10/2021 | Dow et al. | |

FOREIGN PATENT DOCUMENTS

| | | |
|---|---|---|
| CN | 1528313 A | 9/2004 |
| CN | 1528328 A | 9/2004 |
| IN | 2461/MUM/2009 | 3/2012 |
| WO | 0047211 | 8/2000 |
| WO | 2004/058262 A1 | 7/2004 |
| WO | 2012/051614 A2 | 4/2012 |
| WO | 2012/061630 A2 | 5/2012 |
| WO | 2012/087443 A1 | 6/2012 |
| WO | 2016/205001 A1 | 12/2016 |

OTHER PUBLICATIONS

Fabior® (Tazarotene) Foam 0.1% [package insert]. Research Triangle Park, NC: Stiefel Laboratories, Inc; 2012 (Year: 2012).*
Singh et al., Dosage Forms: Non-Parenteral in Encyclopedia of Pharmaceutical Technology, 2002, Marcel Dekker (Year: 2002).*
Flume et al., Int J Toxicol. Jul.-Aug 2012;31(4 Suppl):5S-76S.*
International Search Report and Written Opinion of PCT/US18/32359 of the International Searching Authority completed Jul. 17, 2018 (10 pages).
Kircik, Leon H.: "Tretinoin microsphere gel pump 0.04% versus tazarotene cream 0.05% in the treatment of mild-to-moderate facial acne vulgaris.", Journal of Drugs in Dermatology: JDD, Jul. 2009, vol. 8, No. 7, pp. 650-654.
Shalita A R et al.: "Tazarotene gel is safe and effective in the treatment of acne vulgaris: a multicenter, double-blind, vehicle-controlled study.", Cutis, Jun. 1999,vol. 63, No. 6, pp. 349-354.
Lebwohl et al.: "Duration of improvement in psoriasis after treatment with tazarotene 0.1% gel plus clobetasol propionate 0.05% ointment: comparison of maintenance treatments." International Journal of Dermatology (Jan. 2001) vol. 40, No. 1, pp. 64-66 (XP009191230).
Dhawan et al.: "Tazarotene cream (0.1%) in combination with betamethasone valerate foam (0.12%) for plaque-type psoriasis", Journal of Drugs in Dermatology, New York NY, vol. 4, No. 2, Mar. 1, 2005, pp. 228-230 (XP009159245).
Tazorac® Brochure (ALLERGAN packaging insert, revised Jul. 2017, 13 pages).
International Search Report and Written Opinion of PCT/US16/035991 of the International Searching Authority completed Aug. 6, 2016 (10 pages).

(Continued)

*Primary Examiner* — Kathrien A Cruz
(74) *Attorney, Agent, or Firm* — Kilpatrick Townsend & Stockton LLP (57) ABSTRACT

Topical pharmaceutical compositions include tazarotene or a pharmaceutically acceptable salt of tazarotenic acid and an oil-in-water emulsion vehicle that forms a lotion. The compositions are used to treat skin diseases, such as acne vulgaris.

11 Claims, 10 Drawing Sheets

(56) References Cited

OTHER PUBLICATIONS

Hecker et al., In vitro compatibility of tazarotene with other topical treatments of psoriasis, pp. 1008-1011, Jun. 2000, Elsevier, US.
Allergan. "Drug Approval Package", Medical Review(s) on Tazorac™ cream, part 1, Sep. 25, 2000, 32 pages.
Medical Review, Part 2. Drug Approval Package for Tazorac (tazarotene cream). Application No. 021184. Approval Date: Sep. 29, 2000. accessdata.fda.gov/drugsatfda_docs/nda/2000/21-184_Tazorac.cfm.
Tazorac (Highlights of Prescribing Information, Label (fda.gov), Dec. 2013), 14 pages.

* cited by examiner

TOPICAL COMPOSITIONS AND METHODS FOR TREATING SKIN DISEASES

CROSS REFERENCE TO RELATED APPLICATIONS

This application is a continuation-in-part application of U.S. patent application Ser. No. 15/977,088, filed May 11, 2018, which claims priority to U.S. Provisional Patent 62/505,421, filed May 12, 2017.

BACKGROUND

The present invention relates to topical compositions and methods for treating skin diseases such as acne and psoriasis. In particular, this invention relates to topical pharmaceutical compositions comprising tazarotene or a pharmaceutically acceptable tazarotenic acid salt, in an oil-in-water emulsion vehicle, for treating skin diseases.

The retinoid tazarotene has been commercially available and has been used to treat acne and psoriasis topically. However, tazarotene may cause significant local skin irritation, especially early in the first through fourth weeks of therapy, thus limiting its use for a prolonged period because many patients stop treatment due to skin irritation. The need exists for more effective and safer topical medicaments with reduced adverse effects for the management of acne, psoriasis and other skin diseases.

SUMMARY OF THE INVENTION

In general, the present invention provides topical compositions and methods for treating skin diseases such as acne and psoriasis.

In one aspect, this invention provides a topical pharmaceutical composition for treating skin diseases, including acne and psoriasis, comprising: tazarotene or a pharmaceutically acceptable tazarotenic acid salt present in the composition at a positive concentration of less than 0.050 percent by weight of the composition; and a dermatologically acceptable oil-in-water emulsion vehicle.

In another aspect, this invention provides a method of treating skin diseases, including acne and psoriasis, comprising topically applying a pharmaceutical composition to an affected area of a body of a subject suffering from the skin disease, wherein the composition comprises: tazarotene or a pharmaceutically acceptable tazarotenic acid salt present in the composition at a positive concentration of less than 0.050 percent by weight of the composition; and a dermatologically acceptable oil-in-water emulsion vehicle.

According to other aspects, the topical pharmaceutical composition may comprise tazarotene or the salt thereof at 0.01 to 0.049 percent by weight of the composition, or at about 0.045 percent by weight of the composition.

According to another aspect, the tazarotene or tazarotenic acid salt may be dissolved in a liquid oil component of the emulsion.

According to another aspect, the topical pharmaceutical composition may contain the tazarotene or the tazarotenic acid salt as a sole active pharmaceutical ingredient.

According to various aspects, the oil phase of the emulsion may comprise a liquid oil component comprising a DCAE, a MCAE, or combinations thereof. In other aspects, the oil phase includes diethyl sebacate as the DCAE.

According to other aspects, the aqueous phase of the emulsion may comprise water and a carbomer homopolymer.

According to another aspect, the topical pharmaceutical composition may comprise: an aqueous phase comprising water, a carbomer homopolymer, and a polymeric emulsifier; an oil phase comprising at least one member selected from the group consisting of a dicarboxylic acid ester and a mineral oil, and the tazarotene or the tazarotenic acid salt. According to other aspects, the aqueous phase may further comprise a humectant or a preservative, such as at least one member selected from the group consisting of methylparaben, propylparaben and sorbitol.

According to other aspects, the topical pharmaceutical composition may have the form of a lotion, or of a cream.

According to another aspect, the topical pharmaceutical composition may have a pH of about 4 to about 6.

For the methods of this invention, the step of applying may be carried out once per day for at least eight weeks. According to one aspect, the applying is carried out once per day for at least twelve weeks.

According to other aspects, the composition may be applied is to an affected area of a body of a subject suffering from acne vulgaris in order to treat that condition.

Other features and advantages of the present invention will become apparent from the accompanying drawings and the following detailed description and claims.

DETAILED DESCRIPTION OF THE INVENTION

In general, the present invention provides topical compositions and methods for treating skin diseases, including acne and psoriasis.

Throughout this disclosure, unless otherwise indicated, the concentration of an ingredient of the composition is in percent by weight of the total composition.

In one aspect, the topical pharmaceutical composition comprises tazarotene, or a pharmaceutically acceptable salt of tazarotenic acid, at a concentration below that which is presently utilized in topical formulations. For example, tazarotene or the tazarotenic acid salt is included in a composition at a positive concentration less than 0.05 wt %.

In certain embodiments of the present invention, tazarotene or the tazarotenic acid salt is present in the composition at a positive concentration of less than 0.05% based on the weight of the composition ("wt %"). For example, this component is present in the range from about 0.01 to about 0.049 wt %, or from about 0.01 to about 0.045 wt %, or from about 0.02 to about 0.045 wt %, or from about 0.03 to about 0.045 wt %, or at about 0.045 wt %. Specific concentrations of this component may be 0.01 wt %, 0.015 wt %, 0.02 wt %, 0.025 wt %, 0.03 wt % 0.035 wt %, 0.04 wt %, and 0.045 wt %.

In one aspect, the topical pharmaceutical composition comprises an oil-in-water emulsion as a carrier vehicle, in which an internal oil phase is dispersed in a continuous aqueous phase. The emulsion may be a macroemulsion, a microemulsion, or a nanoemulsion. The composition may have the dosage form of gel, lotion, or cream, or ointment, or liquid, or oil, or spray or foam.

In addition to the tazarotene active ingredient, the composition of the present invention may comprise one or more dermatologically acceptable excipients, such as liquid oils, waxes viscosity-modifying agents, thickening agents, gelling agents, alcohols, surfactants, chelating agents, buffers, preservatives, humectants, emollients, stabilizers, diluents, dispersing agents, emulsifiers, wetting agents, stabilizers, pH adjusters, solvents or cosolvents.

The composition of the invention may desirably contain a thickening agent to provide viscosity so that the formulation may be provided in the form of a gel, lotion, cream, or ointment. The thickening agent may be miscible or soluble in an aqueous fluid. Non-limiting examples of suitable thickening agents include acacia, alginic acid and its salts, hyaluronic acid and its salts, carbomers (also known as carboxy vinyl polymers, which are cross-linked polyacrylic acid), carboxymethylcellulose, ethylcellulose, gelatin, hydroxyethyl cellulose, hydroxypropyl cellulose, hydroxypropylmethyl cellulose, methylcellulose, poloxamers, polyvinylpyrrolidone, polyvinyl alcohol, tragacanth, xanthan gum, magnesium aluminum silicate, and bentonite. The thickening agent may also reside in the oil or lipophilic portion of the formulation. Examples of suitable lipophilic thickening agents include cetyl alcohol, stearyl alcohol, glyceryl stearate, white beeswax, microcrystalline wax, hydrogenated polyisobutane polymers, and emulsifying wax.

A suitable group of thickening agents is carbomers, such as Carbopol® and polycarbophil (The Lubrizol Corporation, Wickliffe, Ohio). Carbopol® homopolymers are polymers of acrylic acid crosslinked with allyl sucrose or allylpentaerythritol. Carbopol® copolymers are polymers of acrylic acid and $C_{10}$-$C_{30}$ alkyl acrylate crosslinked with allylpentaerythritol. Carbopol® interpolymers are carbomer homopolymers or copolymers that contain a block copolymer of polyethylene glycol and a long chain alkyl acid ester. Noveon® polycarbophil is a polymer of acrylic acid crosslinked with divinyl glycol.

A surfactant or emulsifier is optionally included, if desired or required. Pharmaceutically acceptable anionic, cationic, or non-ionic surfactants may be included in a composition of the present invention. Non-ionic surfactants are preferred. Non-limiting examples of non-ionic surfactants are Octoxynol (also known as Macrogol tetramethylbutylphenyl ether, octylphenoxy polyethoxyethanol, or polyoxyethylene octylphenyl ether), such as Octoxynol 1, 3, 5, 8, 9, 10, 12, 13, 16, 30, 40, 70 (wherein the number indicates the number of repeating oxyethylene units), or other Octoxynols that comprise different numbers of repeating units of oxyethylene in the side chain, sorbitan esters (such as sorbitan monooleate and sorbitan monostearate, commonly known by their trade names Span 80 and Span 60), polysorbates (such as polysorbate 80 (polyoxyethylene sorbitan monooleate), polysorbate 60 (polyoxyethylene sorbitan monostearate), polysorbate 20 (polyoxyethylene sorbitan monolaurate), commonly known by their trade names of Tween® 80, Tween® 60, Tween® 20), poloxamers (synthetic block polymers of ethylene oxide and propylene oxide, such as those commonly known by their trade names of Pluronic®; e.g., Pluronic® F127 or Pluronic® F108), or poloxamines (synthetic block polymers of ethylene oxide and propylene oxide attached to ethylene diamine, such as those commonly known by their trade names of Tetronic®; e.g., Tetronic® 1508 or Tetronic® 908, etc.), other nonionic surfactants such as Brij® (polyoxyethylene alkyl ether having a formula of $CH_3$—$(CH_2)_{10\text{-}16}$—(O—$C_2H_4$)$_{1\text{-}25}$—OH), Myrj® (stearic acid esterified with polyoxyethylene having 40-100 repeating oxyethylene units), and long chain fatty alcohols (e.g., oleyl alcohol, stearyl alcohol, myristyl alcohol, docosahexaenoyl alcohol, etc.) with carbon chains having about 12 or more carbon atoms (e.g., such as from about 12 to about 24 carbon atoms).

In addition, polymeric emulsifiers such as those known under the trade name Pemulen™ (The Lubrizol Corporation, Wickliffe, Ohio) may be used. These are polymers of acrylic acid, modified by long chain ($C_{10}$-$C_{30}$) alkyl acrylates, and crosslinked with allylpentaerythritol.

An anionic emulsifier may be used, such as sodium or potassium oleate, triethanolamine stearate, sodium lauryl sulfate, sodium dioctyl sulfosuccinate, and sodium docusate. Less preferred are cationic emulsifiers such as quaternary ammonium salts. Still other emulsifiers include glyceryl monostearate, polyoxyethylene monooleate, polyoxyethylene monostearate, polyoxyethylene monolaurate, potassium oleate, sodium lauryl sulfate, sodium oleate, sorbitan monolaurate, sorbitan monopalmitate, sorbitan monostearate, sorbitan tristearate, sorbitan monooleate, sorbitan trioleate, triethanolamine oleate, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, and polyoxyethylene sorbitan trioleate.

The formulation desirably contains a dermatologically acceptable humectant such as glycerin, sorbitol, hexylene glycol, propylene glycol, or urea. In addition, the formulation may contain an emollient such as petrolatum, lanolin, mineral oil, light mineral oil, stearic acid, cyclomethicone, or dimethicone. Chelating agents such as EDTA and citric acid and their salts may be included in a formulation of the present invention.

The liquid oil component of the composition includes one or more materials that are practically insoluble or insoluble in water and which are liquid at room temperature. For example, in one embodiment, the liquid oil component of the composition includes one or more materials that are practically insoluble or insoluble in water and which are liquid at room temperature of 22° C. The liquid oil component may be selected from one or more ingredients from the group consisting of dicarboxylic acid esters ("DCAE"), monocarboxylic acid esters ("MCAE"), fish-liver oil, long-chain triglycerides (wherein each side chain has 14-18 carbons, such as peanut oil, sesame oil, coconut oil, sunflower oil, corn oil, olive oil, cotton seed oil, or derivatives thereof), propylene glycol diesters, medium-chain triglycerides (such as those wherein each side chains has 8-10 carbons; e.g., capric/caprylic acid triglycerides), hydrocarbons like mineral oil, light mineral oil, squalene, and squalane, fatty alcohols (such as octyldodecanol and isostearyl alcohol), and fatty acids (such as isostearic acid and oleic acid).

In some embodiments, the liquid oil component comprises a dicarboxylic acid ester and light mineral oil. In some other embodiments, the liquid oil component comprises one or more long-chain triglycerides.

The formulation may include other lipophilic liquids in an amount that is sufficient to be miscible with the dicarboxylic acid ester and/or monocarboxylic acid ester. The lipophilic liquid may be an emollient such as lanolin oil, mineral oil, light mineral oil, isostearic acid, squalene, octyldodecanol, fractionated coconut oil, cyclomethicone, or dimethicone.

In addition to the liquid oil component, the formulation may contain water insoluble or practically insoluble ingredients that are not liquid at room temperature, but are soluble in the liquid oil component.

A DCAE that is suitable for the present invention has the formula $R_1OOC-(CH_2)_n-COOR2$, wherein $R_1$ and $R_2$ are alkyl groups containing between 1 and 4 carbons or aryl groups and may be the same or may be different and wherein $(CH_2)_n$ is a straight or branched chain and n is between 1 and 12. Examples of DCAEs containing one or more aryl groups are dibenzyl esters of dicarboxylic acids. A preferred dicarboxylic acid ester is diethyl sebacate, which has the formula $CH_3CH_2OOC-(CH_2)_8-COOCH_2CH_3$. Examples of other suitable dicarboxylic acid esters (where $R_1$ and $R_2$ are the same) are dimethyl, diethyl, dipropyl, diisopropyl, dibutyl and diisobutyl esters such as oxalate, malate, succinate, glutarate, adipate, pimelate, suberate, and azalate. Examples of suitable dicarboxylic acid esters (where $R_1$ is different from $R_2$) are methyl ethyl, methyl propyl, methyl butyl, methyl isopropyl, ethyl propyl, ethyl butyl, ethyl isopropyl, and propyl butyl esters such as oxalate, malate, succinate, glutarate, adipate, pimelate, suberate, azalate, and sebacate.

In some aspects, diethyl sebacate is included at 0.1 to 20 wt %, or at 0.5 to 10 wt %, or at 2 to 4 wt % of the weight of the composition.

Alternatively, or in combination with the DCAE, the formulation may contain a MCAE. The MCAE that is suitable for the present invention has the formula $CH_3-(CH_2)_n-COOR_1$, wherein $R_1$ is an alkyl group containing between 1 and 4 carbons or an aryl group, and wherein $(CH_2)_n$ is straight or branched chain and n is between 1 and 12. Examples of such monocarboxylic acid esters include methyl, ethyl, propyl, isopropyl, butyl, or an aryl such as benzyl formate, acetate, propionate, butyrate, valerate, laurate, myristate, palmitate, and stearate. Examples of preferred monocarboxylic acid esters are isopropyl palmitate and isopropyl myristate.

The liquid oil phase may beneficially be used to dissolve one or more of the active ingredients within the emulsion. In one embodiment the tazarotene component is dissolved in the liquid oil phase within the formulation at room temperature. In another embodiment the tazarotene component is suspended within the formulation at room temperature. In the case wherein the tazarotene component is suspended in the formulation, this suspended active ingredient may be micronized, namely that the mean particle size is preferably about 25 microns in diameter or less.

In one aspect, a composition of the present invention comprises the ingredients at the concentrations shown in Table 1.

TABLE 1

Compositions of the Present Invention for Treating Skin Diseases

| | Concentration (wt %) | | |
|---|---|---|---|
| Ingredient | Range 1 | Range 2 | Range 3 |
| Tazarotene or Tazarotenic Acid Compound | 0.01-0.049 | 0.02-0.045 | 0.03-0.045 |
| Emollient, Solvent, and/or Thickener | 0.5-40 | 1-25 | 2-20 |
| Emulsifier | 0.25-10 | 0.5-7 | 1-5 |
| Humectant | 0-15 | 2-12 | 3-10 |
| Polymeric Thickener | 0.05-2 | 0.1-1.5 | 0.3-1 |
| Pharmaceutical Aids | q.s. | q.s. | q.s. |
| Purified water | q.s. to 100 | q.s. to 100 | q.s. to 100 |

Non-limiting examples of compositions of the present invention are shown in Table 2.

TABLE 2

Some Emulsion Compositions of the Present Invention for Treating Acne

| | | Concentration (wt %) | | | |
|---|---|---|---|---|---|
| Ingredient | Function | Range 1 | Range 2 | Range 3 | Composition A |
| Tazarotene | Retinoid | 0.02-0.049 | 0.03-0.049 | 0.04-0.049 | 0.045 |
| Diethyl sebacate | Liquid Oil & Solvent | 1-5 | 2-4 | 2.5-3.5 | 2.97 |
| Light mineral oil | Liquid Oil & Co-Solvent | 5-15 | 5-10 | 7.5-8.5 | 8.03 |
| Sorbitan monooleate | Surfactant/Emulsifying Agent | 0.01-1 | 0.02-0.5 | 0.05-0.2 | 0.1 |
| Sorbitol solution, 70% | Humectant | 5-15 | 7-12 | 10-11 | 10.7 |
| Methyl paraben | Antimicrobial Preservative[1] | 0.05-0.3 | 0.1-0.3 | 0.1-0.2 | 0.17 |
| Propyl paraben | Antimicrobial Preservative[1] | 0.01-0.1 | 0.01-0.05 | 0.02-0.04 | 0.03 |
| Edetate disodium dihydrate | Chelating Agent[1] | 0.02-0.1 | 0.02-0.7 | 0.03-0.06 | 0.05 |
| Carbomer copolymer type B (e.g., Pemulen ™ TR-1) | Emulsifying Agent | 0.1-1 | 0.2-0.7 | 0.3-0.5 | 0.4 |
| Carbomer homopolymer type A (e.g., Carbomer 981) | Thickener | 0.2-1.5 | 0.3-1 | 0.5-0.7 | 0.6 |
| Sodium hydroxide, 10% Solution | pH-adjusting Agent[1] | q.s. to pH of 5.5 ± 0.5 | q.s. to pH of 5.5 ± 0.5 | q.s. to pH of 5.5 ± 0.5 | q.s. to pH of 5.5 ± 0.5 |
| Purified water | Carrier | q.s. to 100 | q.s. to 100 | q.s. to 100 | q.s. to 100 |

Note:
[1]These ingredients are broadly classified as Pharmaceutical Aids.

A lotion having a composition as shown Composition A of Table 2 may be prepared as follows.

A separate aqueous phase is made. In a manufacturing vessel equipped with a mixing implement (such as a propeller) and temperature control, purified water and disodium edetate dihydrate are combined and the mixture is agitated until a clear solution is achieved. Sorbitol, methylparaben, and propylparaben are then added to the mixture. The mixture is continuously mixed and heated to approximately 75° C. The mixture is agitated until a solution is obtained. The mixture is then removed from the heat source and allowed to cool to below 40° C. with continued mixing. With continuous mixing, Carbopol® 981 and Pemulen™ TR-1 carbomers are added to the mixture and dispersed. Mixing continues until the two carbomers are fully dispersed and hydrated.

A separate oil phase is made. In a vessel equipped with a mixing implement such as a propeller, diethyl sebacate, and tazarotene are combined. The mixture is agitated until a solution is achieved. With continuous mixing, light mineral oil and sorbitan monooleate are added. Mixing is continued until a solution is obtained.

In a separate vessel, an approximate 2.5 N solution of sodium hydroxide is prepared.

With high speed mixing, the oil phase containing the active ingredient (tazarotene) is added to the aqueous phase. Mixing is continued until a homogeneous emulsion is obtained. Mixing speed is decreased and mixing continued for an additional time of 10 minutes to 1 hour. With continuous mixing, an appropriate amount of the sodium hydroxide solution is added incrementally to obtain a pH of 5.5±0.5. Mixing continues further until a homogeneous lotion is obtained, such as for 30 minutes to 3 hours.

A first clinical study in acne patients was conducted to compare the efficacy of a composition of the present invention containing tazarotene (the "Composition A" lotion of Table 2).

A first placebo ("Lotion Placebo") corresponded to and had a similar viscosity as Composition A but lacked tazarotene. A second placebo ("Cream Placebo") corresponded to the Lotion Placebo but employed carbomer homopolymer type C in place of carbomer homopolymer type A to yield a higher viscosity emulsion with a viscosity similar to 0.1% tazarotene cream employed in the study. This allows for better blinding of the test formulations and control of the clinical study. In the following results, data for Lotion Placebo and Cream Placebo may be combined and reported as "Combined Placebo".

Additionally, commercially available 0.1% tazarotene cream (Tazorac® 0.1% cream) was employed in this clinical study for comparison purposes.

A double blind, multi-site, randomized clinical study was conducted on patients suffering from acne vulgaris, whereby neither the acne patient nor the investigator knew the identity of the test composition assigned. 210 patients were randomized to receive either Composition A lotion, Tazorac® 0.1% cream, Placebo Lotion and Placebo Cream at a 2:2:1:1 randomization:
- 69 subjects "Composition A lotion"
- 72 subjects "Tazorac® 0.1% cream"
- 34 subjects "Lotion Placebo"
- 35 subjects "Cream Placebo".

Primary inclusion criteria were moderate to severe acne, inflammatory lesion count of at least 20 but no more than 40, and non-inflammatory lesion count of at least 20 but no more than 100. The blindly labeled lotions were applied to the affected area once daily for twelve weeks, with assessments at 2 weeks, 4 weeks, 8 weeks and 12 weeks.

The investigator monitored the efficacy at each study visit by assessing the treatable area, determining the Evaluator's Global Severity Score (EGSS), and determining the grade of improvement. EGSS included the following grades:
Clear=0; Almost Clear=1; Mild=2; Moderate=3; Severe=4.

Clinical Efficacy was determined primarily based on the percentage of subjects who were treatment successes at 12 weeks. To be judged as a treatment success, as reported in Tables 4, 6, and 7, subjects had to show at least two-grade improvement from the baseline and EGSS score equating to "clear" or "almost clear". Also, the numbers of inflammatory and non-inflammatory lesions were assessed.

Table 3 reports Baseline Characteristics.

TABLE 3

Baseline Characteristics - Inflammatory Lesions and Non-inflammatory lesions

|  | Combined Placebo N = 69 | Composition A N = 69 | Tazorac ® 0.1% Cream N = 72 |
|---|---|---|---|
| Inflammatory Lesions |  |  |  |
| Mean (SD) | 27.2 (5.49) | 28.3 (6.0) | 27.3 (5.95) |
| Median | 26.0 | 27.0 | 26.0 |
| Non-inflammatory Lesions |  |  |  |
| Mean (SD) | 36.6 (13.17) | 37.6 (14.70) | 36.6 (13.31) |
| Median | 34.0 | 34.0 | 34.0 |

Table 4 reports treatment % success on an intention-to-treat (ITT) basis.

TABLE 4

EGSS (Clear or Almost Clear) by Visit (ITT)

|  | Combined Placebo N = 69 | Composition A N = 69 | Tazorac ® 0.1% Cream N = 72 |
|---|---|---|---|
| Week 2 | 0% | 0% | 0% |
| Week 4 | 0% | 1.4% | 1.4% |
| Week 8 | 4.3% | 7.2% | 5.6% |
| Week 12 | 10.1% | 18.8% | 16.7% |

Figure 1:
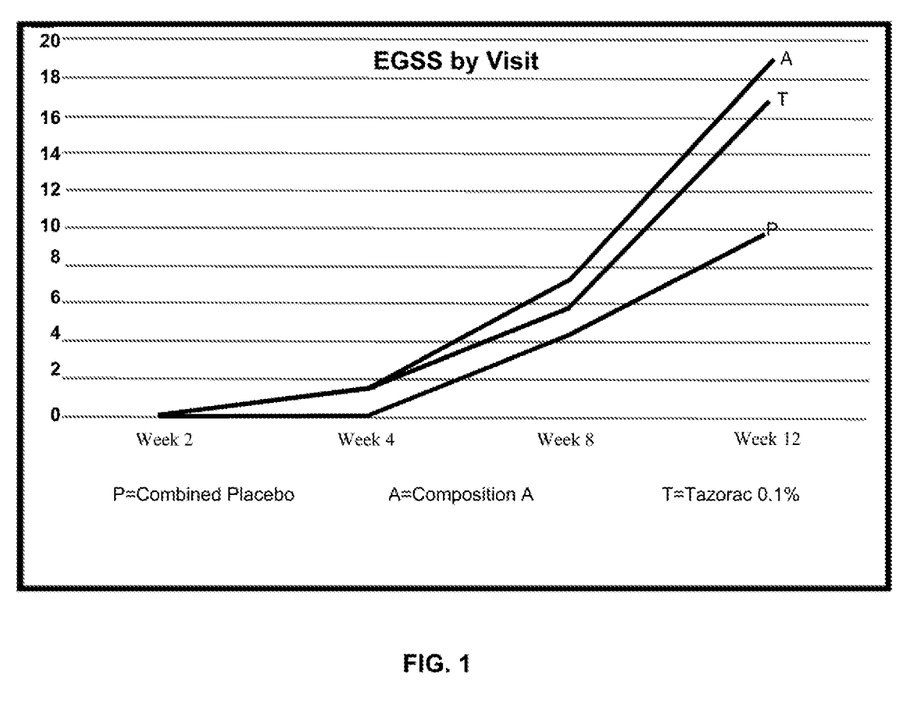
FIG. 1 is a graph of EGSS by visit.
Figure 2:
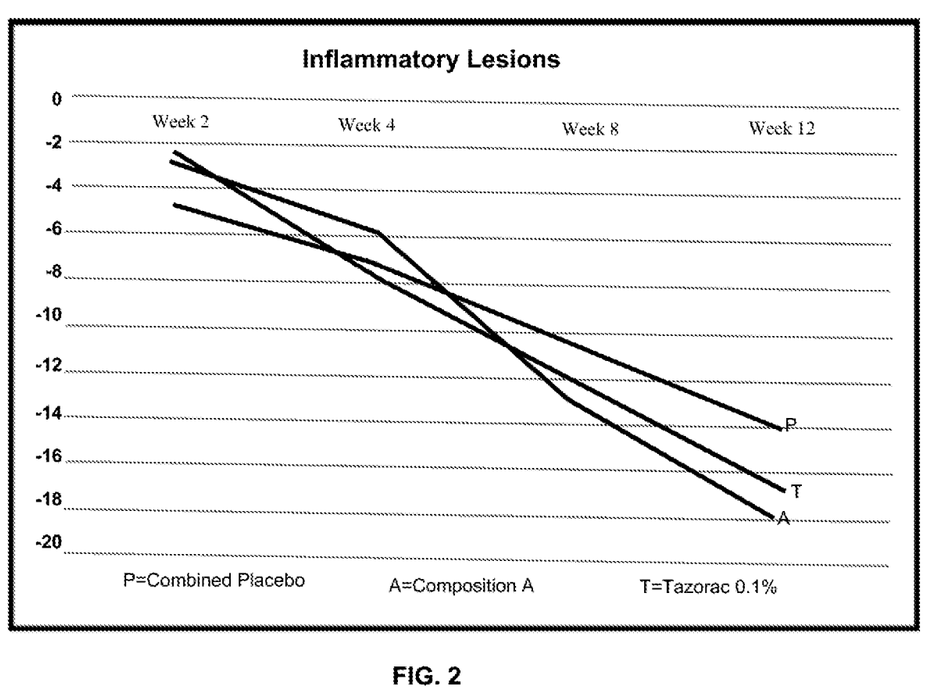
FIG. 2 is a graph of change in inflammatory lesions from baseline.
Figure 3:
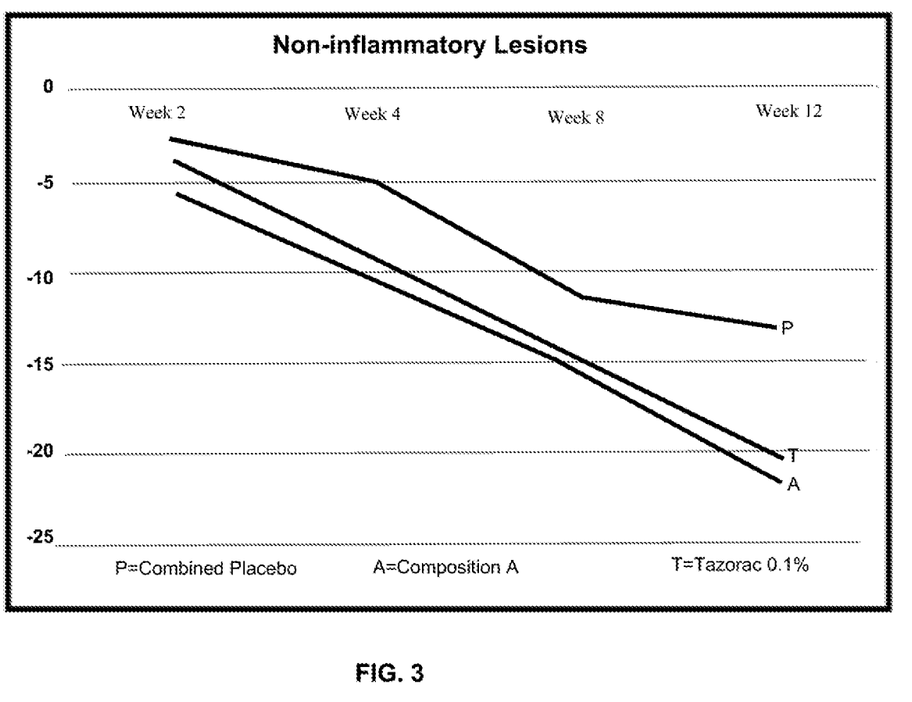
FIG. 3 is a graph of change in non-inflammatory lesions from baseline.

Table 5 reports absolute change in inflammatory lesions from baseline. Change in inflammatory and non-inflammatory lesions from baseline is reported in FIGS. 2 and 3.

TABLE 5

Inflammatory Lesions by Visit Absolute Change from Baseline

|  | Combined Placebo N = 69 | Composition A N = 69 | Tazorac ® 0.1% Cream N = 72 |
|---|---|---|---|
| Week 2 | −4.7 | −2.9 | −2.4 |
| Week 4 | −7.2 | −5.8 | −7.8 |
| Week 8 | −10.9 | −13.2 | −12.0 |
| Week 12 | −14.0 | −18.1 | −16.8 |

Table 6 reports treatment % success for primary efficacy on an intention-to-treat basis for EGSS at week 12. For EGSS, to be judged as a treatment success, subjects had to show at least two-grade improvement from the baseline and EGSS score equating to "clear" or "almost clear". For inflammatory and non-inflammatory lesions, absolute change from baseline to week 12 in mean inflammatory and non-inflammatory counts is reported.

TABLE 6

Treatment % Success (ITT) at 12 Weeks

| | Combined Placebo N = 69 | Composition A N = 69 | Tazorac ® 0.1% Cream N = 72 |
|---|---|---|---|
| EGSS - Clear or Almost Clear | 10.1% | 18.8% | 16.7% |
| Inflammatory Lesions | | | |
| Absolute Change | −14.0 | −18.1 | −16.8 |
| % Change | −51.41% | −63.75% | −59.99% |
| Non-inflammatory Lesions | | | |
| Absolute Change | −13.1 | −21.6 | −20.3 |
| % Change | −35.18% | −56.86% | −54.09% |

Table 7 reports treatment % success on a per-protocol basis for EGSS. For lesions, absolute change from baseline to Week 12 in mean inflammatory and non-inflammatory counts is reported.

TABLE 7

Treatment % Success (PP)

| | Combined Placebo N = 57 | Composition A N = 54 | Tazorac ® 0.1% Cream N = 56 |
|---|---|---|---|
| EGSS - Clear or Almost Clear | 12.3% | 20.4% | 16.1% |
| Inflammatory Lesions | −14.2 | −18.3 | −18.2 |
| Non-inflammatory Lesions | −11.8 | −20.8 | −21.9 |

Figure 4A:
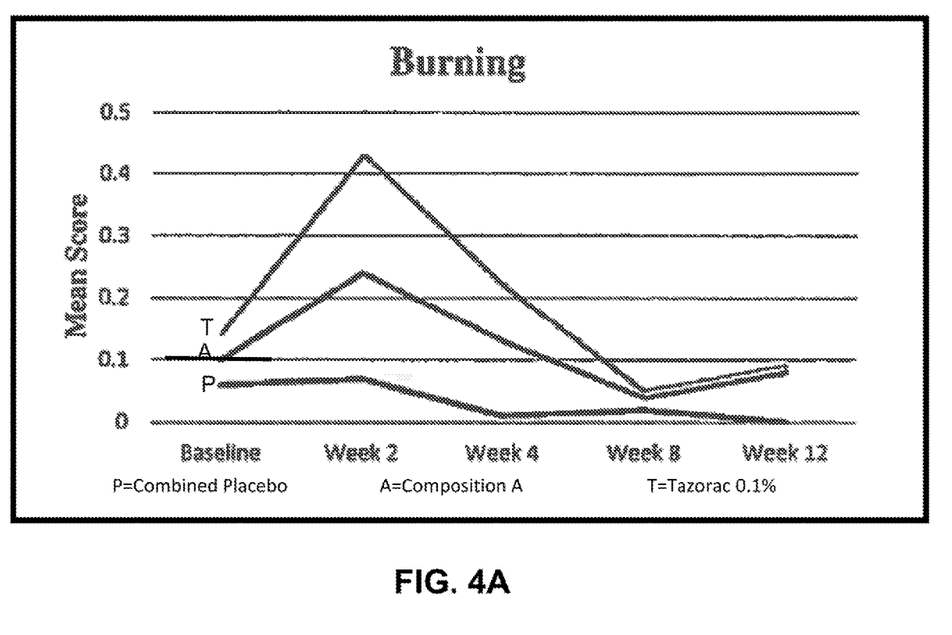
FIGS. 4A, 4B, and 4C are graphs of cutaneous tolerability to burning, stinging, and itching, respectively.
Figure 4B:
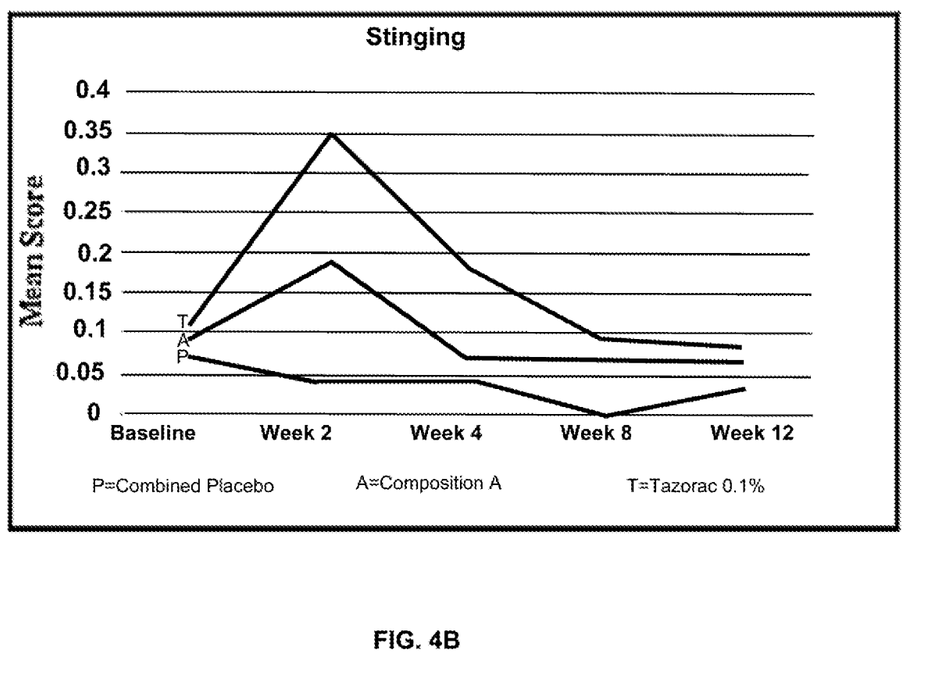
Figure 4C:
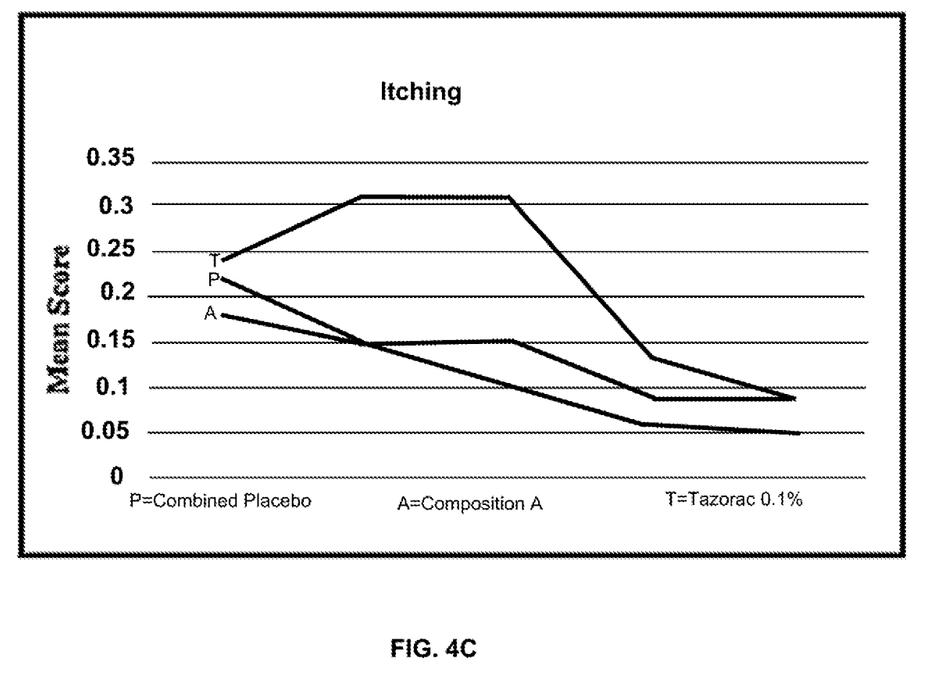
Figure 5A:
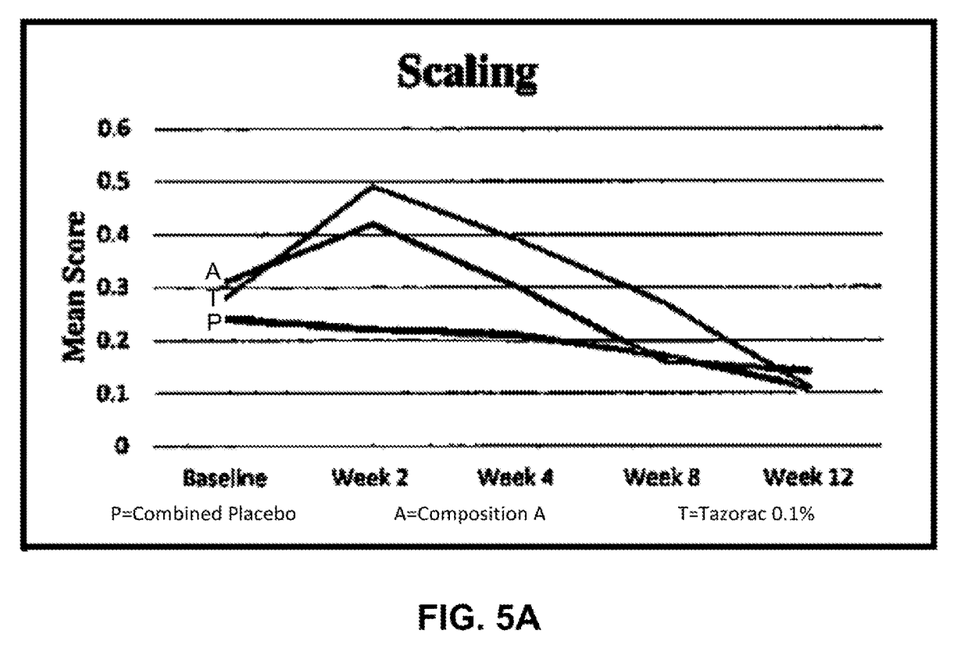
FIGS. 5A, 5B, 5C, and 5D are graphs of cutaneous safety assessed by scaling, erythema, hypo-pigmentation, and hyper-pigmentation, respectively.
Figure 5B:
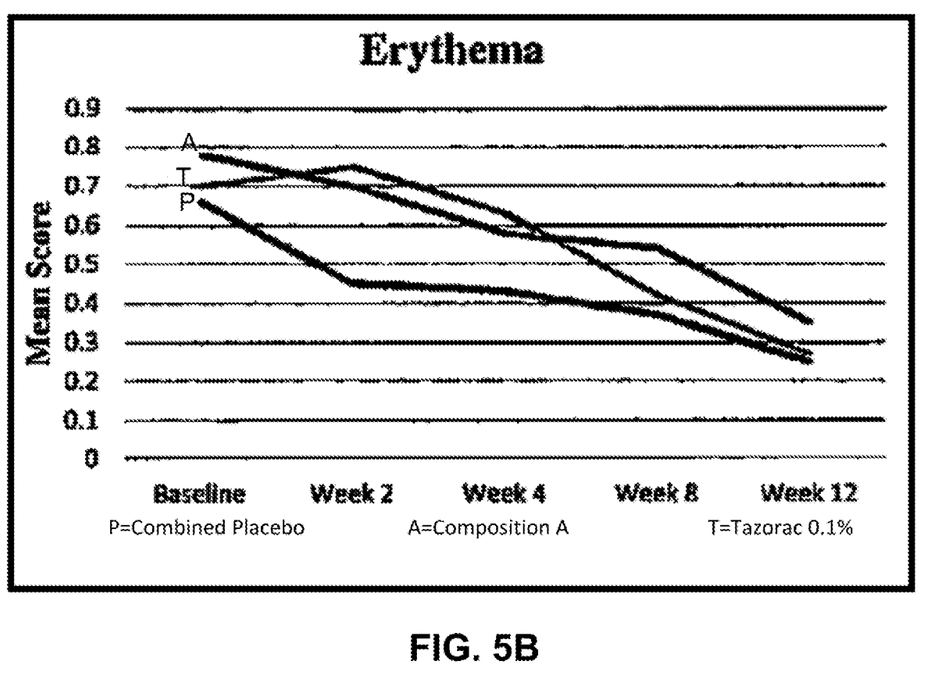
Figure 5C:
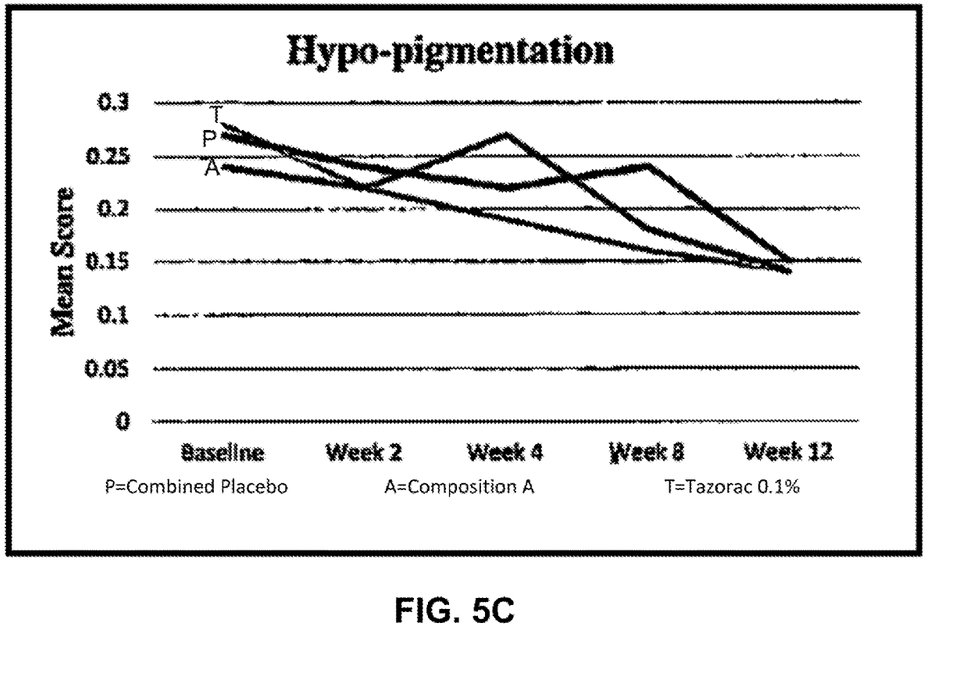
Figure 5D:
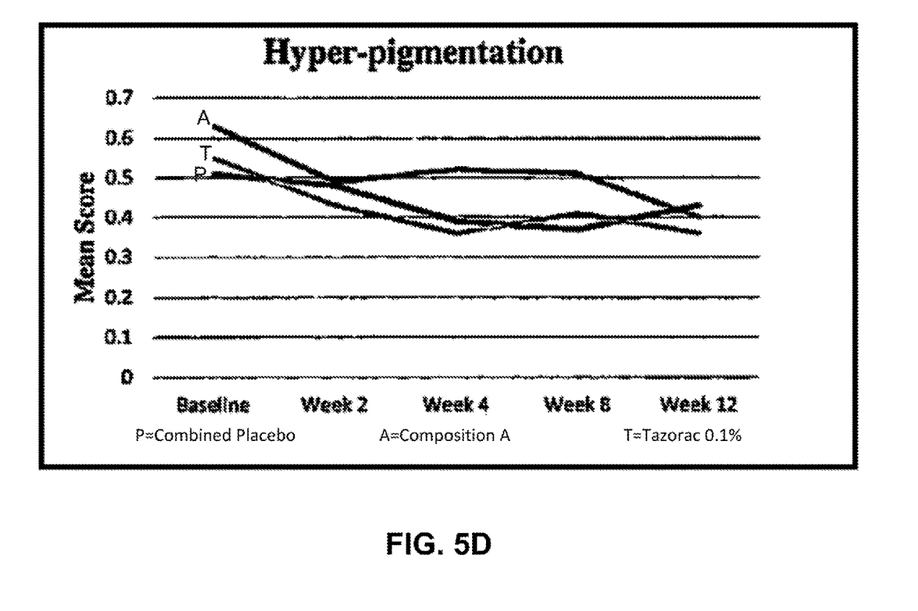

The compositions were tested for cutaneous safety and tolerability. Cutaneous tolerability was assessed by burning, stinging or itching reported by the subjects. This data is summarized in FIGS. 4A, 4B, and 4C. Cutaneous safety was assessed by scaling, erythema, hypo-pigmentation and hyper-pigmentations as evaluated by the investigator. This data is summarized in FIGS. 5A, 5B, 5C, and 5D.

Table 8 reports treatment emergent adverse event characteristics.

TABLE 8

Treatment Emergent Adverse Event Characteristics

| | Combined Placebo | Composition A | Tazorac ® 0.1% Cream |
|---|---|---|---|
| % Subjects Reporting Any Adverse Event | 13.4% | 14.7% | 26.8% |
| % Subjects Reporting Any Serious Adverse Event | 0% | 0% | 0% |
| % Subjects Discontinued Study Due to Adverse Event | 0% | 0% | 1.4% |

Notably, this clinical study showed that Composition A, containing less than half of the tazarotene active ingredient, had a numerically better efficacy than the Tazorac® 0.1% Cream. Also, the adverse event profile was lower for Composition A than for Tazorac® 0.1% Cream.

In another aspect, the present invention provides a method for treating acne. The method comprises topically applying to an affected area of the body of a subject suffering from acne any one of the compositions of the present invention, as disclosed herein, one or more times per day for a period of time sufficient to treat such acne. For example, such a period of time may be 1 to 30 days or longer as needed For example, such a period of time may be one week, two weeks, four weeks, eight weeks, twelve weeks, or longer as needed. For example, a composition of the present invention is applied topically to affected areas of the body once per day for 7-14 days. Alternatively, it may be applied two or three times per day for 7-14 days. Alternatively, it may be applied once per day for one week to six months. For example, it may be applied once per day for two weeks, four weeks, eight weeks, or twelve weeks. In one embodiment, the treatment may be stopped for 1-7 days (e.g., 2, 3, 4, 5, 6, or 7 days) after an extended treatment period before it is resumed for another extended treatment period. Such an extended period may be 7 days, 7-14 days, 7-21 days, 7-30 days, or longer before more treatment is needed or desired.

In yet another aspect, the present invention provides a method of treating acne topically with any of the pharmaceutical compositions of this invention, wherein the composition is applied once daily for more than 2 weeks, such as 4 weeks, for 6 weeks, for 8 weeks or for 12 weeks, without any serious adverse events, and/or with an improved adverse event profile compared to 0.1% tazarotene cream.

In yet another aspect, the present invention provides a method of treating acne topically with any of the pharmaceutical compositions of this invention, wherein the composition is applied once daily for 12 weeks, and has better clinical efficacy and a lower adverse event profile as compared to commercial compositions containing 0.1% tazarotene.

Two larger clinical studies (Studies 301 and 302) in acne patients were conducted to compare the efficacy of a composition of the present invention containing tazarotene (the "Composition A" Lotion of Table 2) to that of a placebo that was the vehicle of Composition A (i.e., without the active ingredient tazarotene).

These studies were phase-3, multi-center, randomized, double-blind, vehicle-controlled, two-arm, parallel group studies comparing the safety and efficacy of Composition A ("IDP-123 Lotion" or "Composition A Lotion") and IDP-123 vehicle lotion ("Placebo Lotion") in the treatment of acne vulgaris. Neither the acne patient nor the investigator knew the identity of the test composition assigned.

In the first study (Study 301), 813 patients were randomized to receive either Composition A Lotion or Placebo Lotion, as follows.
  402 subjects receiving "Composition A Lotion,"
  411 subjects receiving "Placebo Lotion."

In the second study (Study 302), 801 patients were randomized to receive either Composition A Lotion or Placebo Lotion, as follows.
  397 subjects receiving "Composition A Lotion,"
  404 subjects receiving "Placebo Lotion."

Primary inclusion criteria were moderate to severe acne, inflammatory lesion count of at least 20 but no more than 50, and non-inflammatory lesion count of at least 25 but no more than 100. The blindly labeled lotions were applied to the affected facial area once daily for twelve weeks, with assessments at 2 weeks, 4 weeks, 8 weeks and 12 weeks.

The investigator monitored the efficacy at each study visit by assessing the treatable area, determining the Evaluator's Global Severity Score ("EGSS"), and determining the grade of improvement. EGSS included the following grades:
  Clear=0; Almost Clear=1; Mild=2; Moderate=3; Severe=4.

Clinical Efficacy was determined primarily based on: (1) superiority in absolute change from baseline to week 12 in mean inflammatory counts; (2) superiority in absolute change from baseline to week 12 in mean non-inflammatory counts; and (3) percentage of subjects who achieve at least a two-grade reduction from baseline and are "Clear" or "Almost Clear" at week 12 in the EGSS.

Table 9 reports Baseline Characteristics.

TABLE 9

Subject Baseline Characteristics - Inflammatory Lesions and Non-inflammatory Lesion Counts

|  | Study 301 | | Study 302 | |
| --- | --- | --- | --- | --- |
|  | Composition A Lotion N = 402[1] | Placebo Lotion N = 411[1] | Composition A Lotion N = 397[1] | Placebo Lotion N = 404[1] |
| Inflammatory Lesions | | | | |
| Mean (SD) | 28.5(7.04) | 28.1 (7.04) | 28.0 (7.32) | 27.9 (7.10) |
| Median | 26.0 | 26.0 | 26.0 | 26.0 |
| Non-inflammatory Lesions | | | | |
| Mean (SD) | 41.1 (15.67) | 40.7 (16.29) | 41.8 (17.87) | 40.6 (16.31) |
| Median | 36.0 | 34.0 | 36.0 | 35.0 |

Table 10 reports treatment % success at week 12 on an intention-to-treat (ITT) basis.

TABLE 10

EGSS (Clear or Almost Clear) at Week 12 (ITT)

|  | Study 301 | | Study 302 | |
| --- | --- | --- | --- | --- |
|  | Composition A Lotion N = 402 | Placebo Lotion N = 411 | Composition A Lotion N = 397 | Placebo Lotion N = 404 |
| Week 12 | 25.5% (p < 0.001) | 13.0% | 29.6% (p < 0.001) | 17.3 |

Table 11 reports absolute changes in inflammatory and non-inflammatory lesions from baseline at week 12.

TABLE 11

Inflammatory and Non-Inflammatory Lesions Absolute Changes from Baseline at Week 12

|  | Study 301 | | Study 302 | |
| --- | --- | --- | --- | --- |
|  | Composition A Lotion N = 402 | Placebo Lotion N = 411 | Composition A Lotion N = 397 | Placebo Lotion N = 404 |
| Inflammatory Lesions | −15.6 (p < 0.001) | −12.4 | −16.7 (p < 0.001) | −13.4 |
| Non-inflammatory Lesions | −21.0 (p < 0.001) | −16.4 | −24.6 (p < 0.001) | −16.6 |

Table 12 reports assessment of treatment success on a per-protocol basis for EGSS. For lesions, absolute changes from baseline to week 12 in mean inflammatory and non-inflammatory counts are reported.

TABLE 12

Treatment Success (Per-Protocol Basis)

|  | Study 301 | | Study 302 | |
| --- | --- | --- | --- | --- |
|  | Composition A Lotion N = 402 | Placebo Lotion N = 411 | Composition A Lotion N = 397 | Placebo Lotion N = 404 |
| EGSS - Clear or Almost Clear | 26.8% | 14.4% | 30.6% | 18.3% |
| Inflammatory Lesions | −15.8 | −12.4 | −16.4 | −13.4 |
| Non-inflammatory Lesions | −21.3 | −16.3 | −24.1 | −15.4 |

The compositions were tested for cutaneous safety and tolerability. Cutaneous tolerability was assessed by itching, burning, or stinging reported by the subjects. Cutaneous safety was assessed by scaling, erythema, hypo-pigmentation, and hyper-pigmentations, as evaluated by the investigator.

Table 13 shows the number of subjects reporting moderate or severe itching, burning, or stinging; or being observed to have moderate or severe scaling, erythyma, hypopigmentation, or hyperpigmentation. In general, the reported numbers of these conditions are similar between those subjects using Composition A Lotion and Placebo Lotion.

TABLE 13

Cutaneous Safety and Tolerability

|  | Study 301 | | Study 302 | |
| --- | --- | --- | --- | --- |
|  | Composition A Lotion N = 387 | Placebo Lotion N = 392 | Composition A Lotion N = 392 | Placebo Lotion N = 399 |
| Scaling | | | | |
| Moderate | 4 | 2 | 6 | 1 |
| Severe | 0 | 0 | 1 | 0 |
| Erythema | | | | |
| Moderate | 7 | 8 | 13 | 6 |
| Severe | 0 | 0 | 1 | 0 |
| Hypopigmentation | | | | |
| Moderate | 1 | 1 | 0 | 0 |
| Severe | 0 | 0 | 0 | 0 |
| Hyperpigmentation | | | | |
| Moderate | 7 | 9 | 8 | 17 |
| Severe | 1 | 2 | 0 | 1 |
| Itching | | | | |
| Moderate | 4 | 2 | 4 | 4 |
| Severe | 0 | 0 | 0 | 0 |
| Burning | | | | |
| Moderate | 2 | 0 | 5 | 0 |
| Severe | 0 | 0 | 2 | 0 |
| Stinging | | | | |
| Moderate | 1 | 1 | 3 | 0 |
| Severe | 0 | 0 | 1 | 0 |

Table 13 reports treatment emergent adverse event characteristics.

TABLE 13

Treatment Emergent Adverse Event Characteristics

|  | Study 301 | | Study 302 | |
| --- | --- | --- | --- | --- |
|  | Composition A Lotion N = 392[1] | Placebo Lotion N = 399[1] | Composition A Lotion N = 387[1] | Placebo Lotion N = 392[1] |
| % Subjects Reporting Any Adverse Event | 25.5% | 19.5% | 28.2% | 18.6% |
| % Subjects Reporting Any Serious Adverse Event | 0.8% | 0.8% | 0.3% | 0.3% |
| % Subjects Discontinued Study Due to Adverse Event | 3.1% | 0.5% | 2.6% | 0.5% |

Note:
[1]safety population, which comprises all randomized subjects who were presumed to have used the study drug at least once and who provided at least one post-baseline safety evaluation.

Notably, these clinical studies showed that the percentages of subjects reporting any serious adverse event for Composition A are no higher than those for the Placebo Lotion, indicating the excellent safety of Composition A.

The treatment success, as measured by investigator's global assessment of Composition A Lotion (denoted as "EGSS" above) and some commercial products containing a retinoid (as gleaned from their package inserts) is shown in Table 14.

TABLE 14

Comparison of Treatment Success of Various Products Containing a Retinoid

|  |  | Number of Subjects | Treatment Success (%) |
| --- | --- | --- | --- |
| Tazarotene Products | Composition A Lotion, 0.045% tazarotene | 402 | 25.5 |
|  |  | 397 | 29.6 |
|  | Tazorac Cream, 0.1% tazarotene | 218 | 18 |
|  |  | 206 | 20 |
|  | Fabior Foam, 0.1% tazarotene | 371 | 29 |
|  |  | 373 | 28 |
| Tretinoin Products | Altreno Lotion, 0.05% tretinoin | 406 | 16.5 |
|  |  | 413 | 19.8 |
|  | Atralin Gel, 0.05% tretinoin | 375 | 21 |
|  |  | 299 | 23 |
| Adapalene Products | Adapalene Gel, 0.3% | 258 | 21 |
|  | Adapalene Gel, 0.1% | 261 | 16 |
|  | Adapalene Lotion, 0.1% | 533 | 26.3 |
|  |  | 535 | 24.1 |
|  | Epiduo Gel, 0.1% adapalene/2.5% benzoyl peroxide | 149 | 21.5 |
|  |  | 415 | 30.1 |
|  | 0.1% Adapalene in Epiduo vehicle | 148 | 12.2 |
|  |  | 420 | 19.8 |

Surprisingly, Composition A Lotion achieved at least similar or higher success rate than other products that contain at least twice the concentration of the active ingredient.

In another aspect, the present invention provides a method for treating acne vulgaris (acne). The method comprises topically applying to an affected area of the body of a subject suffering from acne any one of the compositions of the present invention, as disclosed herein, one or more (such as 1, 2, 3, or more) times per day for a period of time sufficient to treat such acne vulgaris. For example, such a period of time may be 1 to 30 days or longer as needed. For example, such a period of time may be one week, two weeks, four weeks, eight weeks, twelve weeks, or longer as needed. For example, a composition of the present invention is applied topically to affected areas of the body once per day for 7-14 days. Alternatively, it may be applied two or three times per day for 7-14 days. Alternatively, it may be applied once per day for one week to six months. For example, it may be applied once per day for two weeks, four weeks, eight weeks, or twelve weeks. In one embodiment, the treatment may be stopped for 1-7 days (e.g., 2, 3, 4, 5, 6, or 7 days) after an extended treatment period before it is resumed for another extended treatment period. Such an extended period may be 7 days, 7-14 days, 7-21 days, 7-30 days, or longer before more treatment is needed or desired.

In yet another aspect, the present invention provides a method of treating acne vulgaris topically with any of the pharmaceutical compositions of this invention, wherein the composition is applied once daily for more than 2 weeks, such as 4 weeks, for 6 weeks, for 8 weeks or for 12 weeks, without any serious adverse events, and/or with an improved adverse event profile compared to 0.1% tazarotene cream.

In yet another aspect, the present invention provides a method of treating acne vulgaris topically with any of the pharmaceutical compositions of this invention, wherein the composition is applied once daily for 12 weeks, and has better clinical efficacy and a lower adverse event profile as compared to commercial compositions containing 0.1% tazarotene (Tazorac® Cream).

While the present disclosure shows and describes a number of exemplary embodiments, it will be manifest to those skilled in the art that various further modifications may be made without departing from the spirit and scope of the underlying inventive concept and that the same is not limited to particular compositions, processes, methods, or structures herein shown and described.

What is claimed is:

1. A method of treating acne vulgaris, the method comprising topically applying a pharmaceutical composition once per day to an affected area of a body of a subject suffering from acne vulgaris, wherein:
   the composition comprises tazarotene at a concentration of about 0.045 percent by weight of the composition as a sole active pharmaceutical ingredient
   the composition is an oil-in-water emulsion lotion comprising an oil phase and an aqueous phase;
   the oil phase comprises a dicarboxylic acid ester and a mineral oil at a total concentration of 10-12 percent by weight of the composition;
   the aqueous phase comprises water and a carbomer homopolymer, wherein the concentration of the carbomer homopolymer is 0.5-0.7 percent by weight of the composition; and
   the composition further comprises a polymeric emulsifier at a concentration of 0.3-0.5 percent by weight of the composition.

2. The method of claim 1, wherein the dicarboxylic acid ester in the oil phase is diethyl sebacate.

3. The method of claim 1, wherein the oil phase comprises diethyl sebacate and light mineral oil.

4. The method of claim 1, wherein said applying is carried out for at least eight weeks.

5. The method of claim 1, wherein said applying is carried out for at least twelve weeks.

6. The method of claim 1, wherein said applying is carried out for twelve weeks.

7. The method of claim 1, wherein the tazarotene is in solution in the oil phase of the oil-in-water emulsion lotion.

8. The method of claim 1, wherein the composition has a pH of about 4 to about 6.

9. The method of claim 1, wherein the composition consists essentially of:
0.045 weight % tazarotene;
diethyl sebacate;
light mineral oil;
sorbitan monooleate;
sorbitol solution, 70%;
methylparaben;
propylparaben;
edetate disodium dihydrate;
carbomer polymer type B;
carbomer homopolymer type A;
sodium hydroxide;
purified water.

10. The method of claim 1, wherein the composition consists essentially of:
0.045 weight % tazarotene;
2.5-3.5 weight % diethyl sebacate;
7.5-8.5 weight % light mineral oil;
0.05-0.2 weight % sorbitan monooleate;
10-11 weight % sorbitol solution, 70%;
0.1-0.2 weight % methylparaben;
0.02-0.04 weight % propylparaben;
0.03-0.06 weight % edetate disodium dihydrate;
0.3-0.5 weight % carbomer polymer type B;
0.5-0.7 weight % carbomer homopolymer type A;
sodium hydroxide, q.s. to pH 5.5±0.5; and
purified water, q.s. to 100 weight %.

11. A method of treating acne vulgaris, the method comprising topically applying a pharmaceutical composition to an affected area of a body of a subject suffering from acne vulgaris; wherein the composition consists essentially of:
0.045 weight % tazarotene;
2.97 weight % diethyl sebacate;
8.03 weight % light mineral oil;
0.1 weight % sorbitan monooleate;
10.7 weight % sorbitol solution, 70%;
0.17 weight % methylparaben;
0.03 weight % propylparaben;
0.05 weight % edetate disodium dihydrate;
0.4 weight % carbomer polymer type B;
0.6 weight % carbomer homopolymer type A;
sodium hydroxide, q.s. to pH 5.5±0.5; and
purified water, q.s. to 100 weight %.

* * * * *

UNITED STATES PATENT AND TRADEMARK OFFICE
CERTIFICATE OF CORRECTION

PATENT NO. : 11,311,482 B2
APPLICATION NO. : 16/179561
DATED : April 26, 2022
INVENTOR(S) : Arturo Angel and Radhakrishnan Pillai It is certified that error appears in the above-identified patent and that said Letters Patent is hereby corrected as shown below:

In the Claims

Column 15, Claim 9, Line 13: Delete "carbomer polymer type B" and insert in its place --carbomer copolymer type B--.

Column 16, Claim 10, Line 3: Delete "0.3-0.5 weight % carbomer polymer type B" and insert in its place --0.3-0.5 weight % carbomer copolymer type B--.

Column 16, Claim 11, Line 19: Delete "0.4 weight % carbomer polymer type B" and insert in its place --0.4 weight % carbomer copolymer type B--.

Signed and Sealed this
Fourteenth Day of March, 2023

Katherine Kelly Vidal
*Director of the United States Patent and Trademark Office*